US010024485B2

(12) United States Patent
Abri et al.

(10) Patent No.: US 10,024,485 B2
(45) Date of Patent: Jul. 17, 2018

(54) CARRIER APPARATUS FOR AN OPERATING ROOM

(75) Inventors: Omid Abri, Berlin (DE); Stephan Schrader, Berlin (DE); Thorsten Karge, Berlin (DE); Julian Verkin, Hohen Neuendorf (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 261 days.

(21) Appl. No.: 13/431,679

(22) Filed: Mar. 27, 2012

(65) Prior Publication Data

US 2012/0267499 A1 Oct. 25, 2012

(30) Foreign Application Priority Data

Mar. 30, 2011 (DE) .......... 10 2011 001 681
May 24, 2011 (DE) .......... 10 2011 076 317

(51) Int. Cl.

| | |
|---|---|
| *F16M 11/00* | (2006.01) |
| *F16M 11/04* | (2006.01) |
| *A61B 90/35* | (2016.01) |
| *F16M 11/20* | (2006.01) |
| *F16M 11/38* | (2006.01) |

(Continued)

(52) U.S. Cl.

CPC .......... *F16M 11/046* (2013.01); *A61B 90/30* (2016.02); *A61B 90/35* (2016.02); *A61B 90/37* (2016.02); *A61B 90/50* (2016.02); *F16M 11/048* (2013.01); *F16M 11/2014* (2013.01); *F16M 11/38* (2013.01); *F16M 13/027* (2013.01); *G03B 21/10* (2013.01); *G03B 21/16* (2013.01); *G03B 21/56* (2013.01); *G03B 21/58* (2013.01); *A61B 34/25* (2016.02); *A61B 90/361* (2016.02); *A61B 2090/372* (2016.02); *A61B 2090/401* (2016.02); *A61B 2090/506* (2016.02); *F16M 2200/063* (2013.01); *F16M 2200/066* (2013.01)

(58) Field of Classification Search

CPC ........ A61B 19/00; A61B 6/4464; A61G 3/00; A61G 7/1042; F16M 13/027; F16M 11/425; B65G 37/00; B61B 3/00

USPC ................. 312/247, 209, 306, 312; 108/149, 108/144.11, 145; 104/89–111

See application file for complete search history.

(56) References Cited

U.S. PATENT DOCUMENTS 2,506,086 A * 5/1950 Jess ............................... 312/247
3,004,141 A * 10/1961 Waller ....................... F21S 8/02
  181/293

(Continued)

FOREIGN PATENT DOCUMENTS

| DE | 8710117 U1 | 11/1988 |
| DE | 8913719 U1 | 2/1990 |

(Continued)

OTHER PUBLICATIONS

German Search Report; Application No. DE 10 2011 076 317.1; dated Jan. 16, 2012; 6 pages.

*Primary Examiner* — Daniel J Rohrhoff
(74) *Attorney, Agent, or Firm* — Whitmyer IP Group LLC

(57) ABSTRACT

A carrier apparatus for a medical device in a medical treatment facility includes a device holder that holds a medical device and a container that receives the device holder with a medical device, such that the device holder can move between an upper resting position in the container and a lower operating position in which a medical device held by the device holder can be used by medical staff.

21 Claims, 7 Drawing Sheets

(51) Int. Cl.
*F16M 13/02* (2006.01)
*G03B 21/10* (2006.01)
*G03B 21/16* (2006.01)
*G03B 21/56* (2006.01)
*G03B 21/58* (2014.01)
*A61B 90/30* (2016.01)
*A61B 90/50* (2016.01)
*A61B 90/00* (2016.01)
*A61B 90/40* (2016.01)
*A61B 34/00* (2016.01)

(56) References Cited

U.S. PATENT DOCUMENTS

| | | | | | |
|---|---|---|---|---|---|
| 3,118,066 | A | * | 1/1964 | Thomas | 378/194 |
| 3,345,471 | A | * | 10/1967 | Kilburg | H02G 5/04 |
| | | | | | 104/93 |
| 3,373,285 | A | * | 3/1968 | Barrett | 378/194 |
| 3,550,169 | A | * | 12/1970 | Forse | B65G 37/00 |
| | | | | | 198/465.4 |
| 3,590,173 | A | * | 6/1971 | Stahmer | H02G 5/04 |
| | | | | | 191/23 A |
| 3,603,037 | A | * | 9/1971 | Mann, Jr. | B24C 3/083 |
| | | | | | 451/2 |
| 3,669,288 | A | * | 6/1972 | Young | B65G 1/0414 |
| | | | | | 414/803 |
| 3,902,070 | A | * | 8/1975 | Amor et al. | 378/194 |
| 3,931,452 | A | | 1/1976 | Nilsson | |
| 4,041,320 | A | * | 8/1977 | Amor et al. | 378/194 |
| 4,901,339 | A | * | 2/1990 | Heinz et al. | 378/197 |
| 5,626,504 | A | * | 5/1997 | Liu | A63H 21/02 |
| | | | | | 104/118 |
| 6,027,247 | A | * | 2/2000 | Tachi | A61B 6/0457 |
| | | | | | 378/177 |
| 6,338,573 | B1 | * | 1/2002 | Michioka | F16C 19/362 |
| | | | | | 104/106 |
| 6,349,436 | B1 | * | 2/2002 | Kreuzer | 5/600 |
| 6,364,268 | B1 | | 4/2002 | Metelski | |
| 6,371,637 | B1 | * | 4/2002 | Atchinson | F21V 19/005 |
| | | | | | 362/249.04 |
| 7,377,475 | B1 | * | 5/2008 | Lopez | 248/323 |
| 8,768,545 | B2 | * | 7/2014 | Ikeya | 701/19 |
| 2004/0265112 | A1 | | 12/2004 | Nieuwenhuis | |
| 2005/0031087 | A1 | * | 2/2005 | Maschke | A61B 6/4405 |
| | | | | | 378/196 |
| 2005/0160843 | A1 | * | 7/2005 | Haab et al. | 74/29 |
| 2006/0066188 | A1 | * | 3/2006 | Crawford | 312/247 |
| 2006/0201782 | A1 | * | 9/2006 | Ishikawa | B65G 37/00 |
| | | | | | 198/465.1 |
| 2007/0158522 | A1 | * | 7/2007 | Shahrokhi | 248/429 |
| 2008/0217268 | A1 | * | 9/2008 | Yoshida | H01L 21/67766 |
| | | | | | 211/41.18 |
| 2008/0219000 | A1 | * | 9/2008 | Fan | 362/241 |
| 2008/0247516 | A1 | * | 10/2008 | Fink et al. | 378/194 |
| 2010/0288155 | A1 | * | 11/2010 | Chepurny et al. | 104/89 |
| 2011/0037840 | A1 | * | 2/2011 | Hiltl | A61B 90/35 |
| | | | | | 348/61 |
| 2012/0002409 | A1 | * | 1/2012 | Donauer | 362/218 |

FOREIGN PATENT DOCUMENTS

| | | |
|---|---|---|
| DE | 19719349 A1 | 7/1998 |
| DE | 29903798 U1 | 5/1999 |
| DE | 20001134 U1 | 5/2000 |
| DE | 20102947 U1 | 4/2002 |
| DE | 20219100 U1 | 4/2003 |
| DE | 102008011311 A1 | 9/2009 |
| DE | 202009014932 U1 | 8/2010 |
| WO | 2008128556 A1 | 10/2008 |
| WO | WO 2010131558 A1 * | 11/2010 |

\* cited by examiner

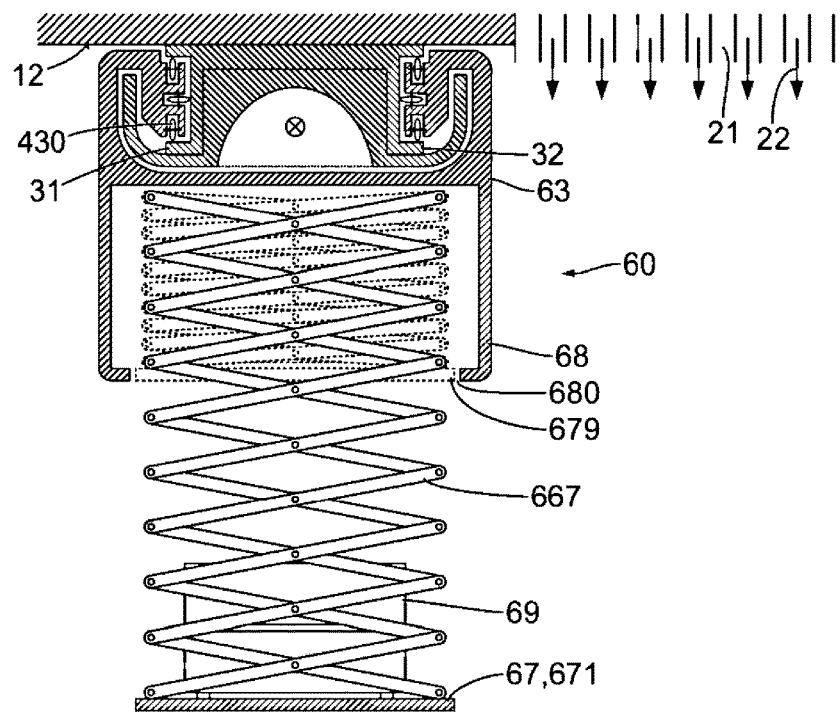
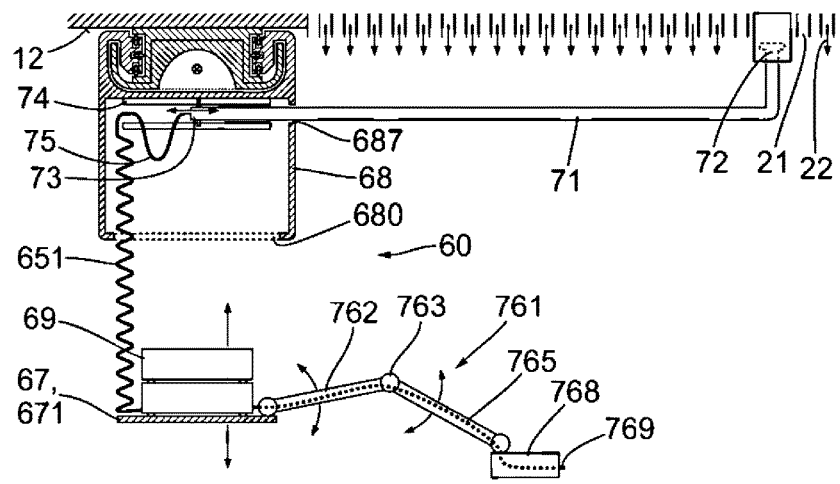

US 10,024,485 B2

CARRIER APPARATUS FOR AN OPERATING ROOM

CROSS-REFERENCE TO RELATED APPLICATIONS

The present application claims priority of German Patent Application Nos. 10 2011 001 681.3 filed on Mar. 30, 2011 and 10 2011 076 317.1 filed on May 24, 2011, the content of which is incorporated herein by reference.

FIELD OF THE INVENTION

The present invention relates to a carrier apparatus for an operating room or other medical treatment facility.

BACKGROUND OF THE INVENTION

The number of devices and systems that are provided in a modern operating room or other medical treatment facility for diagnostic or therapeutic purposes has constantly increased over time. The functions provided by these devices and systems are increasing, and the quantity of information made available to surgical and other staff, and required to be processed by them, is also growing. Therefore there are efforts to integrate functions previously fulfilled by numerous separate devices into fewer devices and systems; to improve the arrangement of devices and systems; to display information, which previously was provided at different locations, in a common location and geared as far as possible to a specific situation, in particular on viewing screens of constantly increasing size; and in general to improve ergonomic qualities.

U.S. Pat. No. 3,931,452 describes an attachment for ceiling-suspended equipment in an operating theater. The stationary ends of girders can be bolted to tracks running in the ceiling, which can also carry cables.

In patent DE 299 03 798 U1, an arrangement is described for moving devices in the clinical area. A powered driver runs along a track mounted on a wall and thus draws a mechanically coupled device, which stands on runner wheels on the floor, from an anesthesiology area, for example, to an operating room.

Patent DE 197 19 349 A1 discloses a medical work area having a mechanically movable projector for projecting images onto a rollable projection surface.

In DE 200 01 134 U1, a surgical system is described having a virtual touch screen, gesture recognition, a video projector and a projection surface. The video projector can be situated on a track device or secured in stationary manner. The video projector and display surfaces can be mechanically movable.

SUMMARY OF THE INVENTION

It is an object of the present invention to make possible improved ergonomy in a medical treatment facility, in particular in an operating room.

This object is fulfilled by the content of the independent claim.

Refinements are indicated in the dependent claims.

Embodiments of the present invention are based on the idea of providing a device holder for a medical device for a medical treatment facility, said device holder being, together with the medical device, vertically movable or transportable between an upper resting position in a container and a lower operating position. The container makes it possible to store a device when not needed so that it is protected from damage or contamination. Vertical mobility of the device between its lower operating position and its upper resting position in the container can permit short-term activation of the device and, likewise on short notice, deactivation or stowage of the device after use.

A carrier apparatus for a medical device in a medical treatment facility includes a device holder that is configured for containing a medical device and a container that is configured to hold the device holder with a medical device, such that the device holder can be moved between an upper resting position in the container and a lower operating position, in which a medical device held by the device holder can be used by medical staff.

The medical treatment facility can be, for example, an operating room. The medical device is a device foreseen for use by medical staff in the context of medical procedures. The device holder is, for example, a shelf-type carrier on which the medical device stands, or a framework or rack container into which the medical device can be inserted. The device holder can be configured to hold several medical devices. The device holder can largely enclose one or more medical devices, such that their user interfaces are accessible, or can keep the device or devices accessible from just about all sides.

The device holder can be moved, in particular, along a predetermined straight and essentially vertical path or (in the context of the precision that is desired and usually obtained) in a precisely vertical path between the upper resting position and the lower operating position.

By arranging the device holder with one or more devices in the upper resting position in the container, said devices are substantially protected from damage and contamination. The simple vertical motion of the operating position allows short-term activation or start-up of one or more devices that are held by the device holder. By means of a contrary vertical motion back into the upper resting position, a likewise short-term deactivation or shutdown of the device becomes possible. Devices that are required only for short terms can be placed, during periods when not needed, in the container, where they cause no disturbance either spatially or visually.

A carrier apparatus as described here can, in addition, comprise a lifting device to move the device holder between the upper resting position and the lower operating position.

The lifting device is configured, in particular, for vertical or essentially vertical movement of the medical device. In particular, the movement between the upper resting position and the lower operating position is essentially vertical when the horizontal distance between the upper resting position and the lower operating position is at most equal in size to (and in particular at most half as large as) the vertical distance between the upper resting position and the lower operating position.

The lifting device includes, in particular, a gas-pressure or other spring and/or an electrical, pneumatic or hydraulic power drive. The gas-pressure or other spring can be configured at least partly to compensate, at least partially, the weight impact of the device holder and of medical devices held by it. This serves to reduce the force required to move the device holder and the medical devices. A controllable mechanical power drive of the lifting device, in addition, allows partly or completely independent movement of the device holder between an upper resting position and a lower operating position.

A carrier apparatus as described here includes, in particular, an opening on the underside of the container so that the device holder can be moved with a medical device through the opening between the resting position and the operating position.

The size of the opening is adapted, in particular, to the device holder and to one or more medical devices that are to be held by the device holder. The device holder can be configured to close the opening when it is situated in its upper operating position. The closing device at the opening can further improve the protection of the device holder and of the medical devices held by the device holder from damage and contamination. In addition, a closing of the opening by the device holder can further relax the optical impression caused by the carrier apparatus and thus improve ergonomy.

With a carrier apparatus as described here, it is possible to provide a movable cover on the container to at least partially close an opening on the underside of the container.

The cover, in particular, can be pivoted or slid between a position or orientation in which it releases the opening and a position or orientation in which it partially or completely closes the opening. The cover can be configured to independently close the opening when the device holder assumes its resting position. The cover and the device holder can be identical or partly or completely integrated, such that the device holder in particular is flat or essentially flat in shape.

A carrier apparatus as described here can, in addition, comprise a steering device to guide the device holder along a predetermined path between the resting position and the operating position.

The predetermined path, in particular, is straight and vertical or essentially vertical. The steering device can be partly or completely integrated with the lifting device.

Guiding the device holder along a predetermined path can improve the operational safety of the carrier apparatus. In addition, the steering device can define the lower operating position of the device holder in the lateral direction and thus simplify the use of a medical device held by the device holder in the operating position.

With a carrier apparatus as described here, the steering device includes, in particular, a scissors mechanism that is configured to hold the device holder in a predetermined orientation independently of its position.

A scissors mechanism, made up of a number of blades crossed in pairs and connected jointedly with one another at their cross-points and their ends, can make possible a defined parallel sliding of the device holder. In particular, the scissors mechanism is configured to hold the device holder horizontally both in its upper resting position and in its lower operating position.

In addition, a scissors mechanism can be part of a lifting device, in such a way that to vertically move the device holder, for example, it is sufficient to exert a force on the topmost pair of blades in relation to one another.

With a carrier apparatus as described here, the steering device can include a telescopable mechanical connection between the container and the device holder.

A telescopable mechanical connection includes in particular one or more series-connected linear guides.

A carrier apparatus as described here can include a cable and a power drive device to move the device holder between the resting position and the operating position by means of the cable.

The power drive device and the cable are, in particular, components of the lifting device or constitute the lifting device. The power drive device includes, for example, an electrical or pneumatic or hydraulic engine with a reel for winding up the cable. Several cables that are moved simultaneously by means of the same reel or by means of several coupled reels that are mechanically connected with one another can ensure a desired orientation of the device holder in every one of its positions.

In a carrier apparatus as described here, the container can be movable parallel to the ceiling surface of the medical treatment facility.

In particular, the container is horizontally movable or drivable on one or more tracks. In particular, the device holder and possibly the lifting device and possibly the steering device can be moved parallel to the ceiling surface of the medical treatment facility. The container can move, in particular, along a path predetermined by a track device of a ceiling supply system, as described above. The partial or complete integration of the carrier apparatus with a ceiling supply system, as described above, makes possible a high-grade mobility of the carrier apparatus without requiring a girder as is customarily regularly used.

A carrier apparatus as described here can, in addition, include a cable for conducting at least either a signal or for current or for a fluid between the container and the device holder or a medical device contained by the device holder.

Current, signals and fluids can thus be conducted from devices held by the device holder via the container or can be removed via the container. Signal lines, lines for transmitting (especially electrical) power and fluids can be in constant connection with medical devices held by the device holder, regardless of the position of the device holder. Thus no installation tasks are required for converting the device holder from its resting position into its operating position or vice versa.

With a carrier apparatus with a cable between the container and the device holder and a steering device as described here, the cable can be integrated into the steering device or guided on the steering device.

Integration of the cable into the steering device or guiding the cable on the steering device can make possible a defined arrangement of the cable and the avoidance of cable loops. Integrating the cable can make it possible to protect the cable from damage, contamination and harmful environmental impacts.

A carrier apparatus as described here can, in addition, include a supply arm that can be rotated around a site determined by a joint, so that the supply arm is coupled with the container of the carrier apparatus on a site at a distance from the joint, and so that the supply arm is configured to transmit at least either a signal or current or a fluid.

The supply arm, in particular when the carrier apparatus is positioned immovably or to be movable along a circular path, can be of rigid configuration. Alternatively, the supply arm can be of pliable or telescopable configuration. A telescopable configuration of the supply arm allows, in particular, for the carrier apparatus to be transported along an elliptical path or other non-circular path.

The site predetermined by the joint is, in particular, positioned approximately in the center of the ceiling surface of the medical treatment facility or in the center of a surface that is circumscribed by the path along which the carrier apparatus can be transported. The joint is, in particular, configured to make possible a rotation or pivoting of the supply arm around a vertical or essentially vertical axis. In addition the joint can make pivoting possible around a horizontal axis.

The supply arm includes, in particular, a first or radially inner end, which comprises the joint, and a second or radially outer end, which is coupled with the container of the carrier apparatus. A jointed coupling of the radially outer end of the supply arm with the container and a slidability of the radially outer end of the supply arm in relation to the container can make it possible to use the supply arm on a non-circular path determined by the track device.

The supply arm comprises, in particular, one or more electrical cables and/or light conductor cables and/or tubes and/or hoses. The supply arm makes it possible to transmit electric power, electrical and optical signals and fluids to or from the container on a circuit around the joint, reliably, without interruption and at least independently of the position of the carrier apparatus.

For this purpose the supply arm comprises, in particular, at the joint or integrated partly or completely into the joint, a rotary union or other device for continuous and uninterrupted electrical or optical transmission of power and/or signals and/or for transmission of one or more fluids or media. The rotary union or other device is configured to make possible a transmission of power, signals and/or fluids or media, independently of the orientation or position of the supply arm and in particular also during a movement or rotation of the supply arm around the joint and in particular also after a rotation around any desired angle.

The rotary union or the other device can comprise one or more insulating devices. Likely insulating devices include, in particular, radial shaft seals (often also known as oil seals), axial wave insulations or other insulating devices that make possible a fluid-tight insulation against the penetration of a fluid. Slip-rings and sliding or slipping contacts can be foreseen for transmitting electrical power or electrical signals.

Alternatively, it is possible to use twistable or windable or spiral-shaped wind-up and unwindable elastic electrical, optical or fluid lines that allow no free choice of rotation but only a rotation bounded by an angle interval. The angle interval can be greater than 360 degrees.

The supply arm, in particular, is not configured to receive the weight impact of the carrier apparatus.

The supply arm thus does not comprise a girder as is very often used customarily for supporting surgical lights, screens and other devices in medical treatment facilities. The supply arm can therefore be set up for markedly lower mechanical impacts and can comprise a clearly smaller cross-section than a conventional girder. In addition, the cross-section of the supply arm can be configured in such a way that the supply arm does not disturb a vertical laminar flow field, or does so only to a minor extent. In particular, the supply arm comprises a cross-section whose width is smaller than (in particular, only half as large as) the height, so that the width is measured in the horizontal direction and the height in the vertical direction. In addition, the supply arm can have a teardrop-shaped cross-section in order to reduce the impact of the supply arm on the vertical laminar flow field.

A ceiling supply system for a medical treatment facility includes a track device that is to be secured on a ceiling surface of the medical treatment facility and that generates a curved path, and a carrier apparatus as described here, such that the container, the lifting device and the device holder can be moved along the path determined by the track device.

BRIEF DESCRIPTION OF THE DRAWINGS

Embodiments are described in closer detail hereinafter with reference to the appended drawings, which are as follows.

FIG. 11 shows a schematic depiction of an additional carrier apparatus.

FIG. 12 shows a schematic depiction of a supply arm.

DETAILED DESCRIPTION OF THE INVENTION

Figure 1:
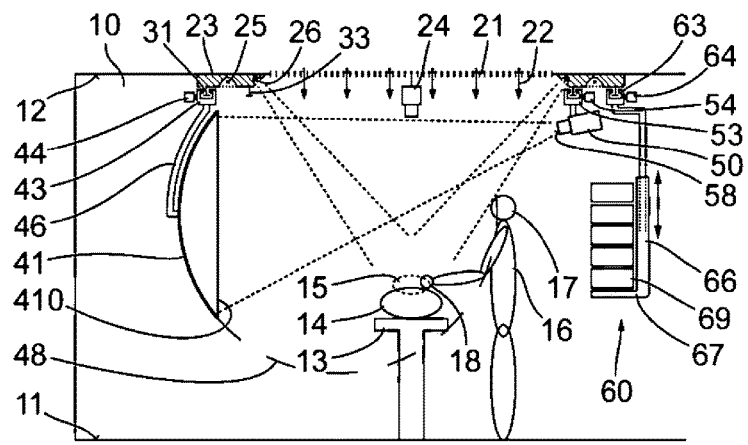
FIG. 1 shows a schematic depiction of a medical treatment facility.

FIG. 1 shows a schematic depiction of a medical treatment facility 10, in particular of an operating room, having a floor surface 11 and a ceiling surface 12. The plane of projection of FIG. 1 is perpendicular to the floor surface 11 and to the ceiling surface 12. The ceiling surface 12, in particular, is level or essentially level and is formed by the underside of the ceiling that is visible from the interior of the medical treatment facility 10. On the floor surface 11 of the medical treatment facility 10 there stands or is affixed a treatment table 13, on which a patient 14 can lie, for example during a surgical procedure. A broken line indicates the outline of a surgical site 15. Alongside the treatment table 13 stands a physician or other medical staff 16 with a head 17. The medical staff 16 holds one hand 18 in the surgical site 15.

In a central area above the treatment table 13, numerous air nozzles 21 are mounted on the ceiling surface 12. The air nozzles 21 are configured, for example, by openings in grids. The air nozzles 21 are configured to generate a vertical laminar flow field 22 of low-dust, low-germ, tempered air, where the low-dust and low-germ air is furnished by a ventilating system that is not shown in the drawings. The area of the ceiling surface 12 occupied by the air nozzles 21 can be, for example, circular, elliptical, square or rectangular and can comprise a total surface of several square meters.

Vertically above the treatment table 13 and the surgical site 15, a room video camera 24 is situated below the ceiling surface 12, in particular immediately below the ceiling surface 12. Contrary to the depiction in FIG. 1, the room camera 24 can be positioned in the ceiling of the medical treatment facility in such a way that only a light inlet surface of the room camera 24 is positioned at the height of the ceiling surface or immediately below it. The room camera 24 can constitute a disturbance of the flow field 22 generated by the air nozzles 21 and is therefore configured as small as possible, in particular, and/or as free-flowing as possible.

The room camera 24 is intended to record the surgical site 15 or to record a larger area that can include the entire treatment table 13 and any medical staff 16 present at the treatment table 13. The room camera 24 can be a time-of-flight camera or a stereo video camera for three-dimensional recording of the surgical site 15 or of a greater area. Instead of a room camera 24 or in addition thereto, several video cameras with different viewing angles and/or with different functions can be provided, for example a time-of-flight camera and a two-dimensional high-resolution camera without recording a third dimension.

The area occupied by the air nozzles 21 on the ceiling surface 12 is surrounded by a ceiling supply system that is, in particular, circular in shape, or a component 23 of a ceiling supply system. Integrated in the ceiling supply system 23 are, in particular, a general illumination 25 for essentially homogeneous illumination of the entire medical treatment facility or of a central area of the medical treatment facility 10 and a surgical light 26 for illuminating the surgical site 15. The surgical light 26 includes, in particular, a number of single emitters, which each generate narrow light cones, and which can be adjustable and/or controllable individually or in groups with respect to the direction of the light emission and/or the intensity or generated light flow and/or with respect to the size of the particular illuminated angle area and/or with respect to the direction of the light emission. In addition, tracks 31, 33 are integrated in the ceiling supply system 23 that each likewise surround in circular shape the area of the ceiling surface 12 occupied by the air nozzles 21. Contrary to the depiction in FIG. 1, the ceiling supply system 23 can be partly or completely integrated in the ceiling of the medical treatment facility 10, so that the underside of the ceiling supply system 23 is shaped flush with the ceiling surface 12.

Several devices, apparatuses or systems are each affixed to one of the tracks 31, 33 or hanging on one of the tracks 31, 33 and can be moved or slid manually or mechanically along the paths parallel to the ceiling surface 12 that are determined by the tracks 31, 33. A few examples are presented hereinafter with reference to FIG. 1 and the other drawings.

One trolley 43 is mounted on the first track 31 of the ceiling supply system 23 and carries a projection surface 41 via a carrier 46. A power drive device 44 is provided on the trolley 43 for electro-mechanical movement of the trolley 43 and, with it, of the carrier 46 and projection surface 41 along the path determined by the first track 31. The projection surface 41 has, in particular, the shape of a portion of a spherical surface or of a surface of a two- or three-axis ellipsoid. The border 410 of the projection surface 41 lies, for example, in a plane and is circular or essentially circular in shape or has the shape of a line of intersection of a cylindrical mantle with a spherical surface, so that the cylinder in particular comprises an essentially rectangular cross-section with rounded corners.

The projection surface 41 is formed by a surface, facing the medical staff 16, of a corresponding body, which for instance is spherical-shell-shaped and whose structural characteristics are not described in further detail here.

An additional trolley 53 can move along the path determined by the second track 33 and carries a projector or a projection system 50 for projecting a moving or non-moving image, a graph, text, figures, symbols and other images of information on the projection surface 41. The projector 50 comprises traits and characteristics, in particular, that with respect to the projection of light are conventionally associated with a video beamer. A power drive device 54 on the other trolley 53 makes possible a mechanical movement of the other trolley 53 and of the projector 50 along the path determined by the second track 33.

The projector 50 and the projection surface 41 together form a display device for displaying medically relevant information for medical staff 16. In addition to the power drive devices 44, 54 on the trolleys 43, 53, other power drive devices can be provided on the projection surface 41 and/or on the projector 50 in order to be able to pivot these in each case in one or more directions, in particular in the horizontal and vertical directions. As a result, the projection surface can be directed at all times at the medical staff 16 and/or at the projector 50 and the projector 50 can be directed at all times at the projection surface 41.

Another trolley 63 on the first track 31 carries a carrier apparatus 60 for one or more medical devices 69. The other trolley 63 and with it the carrier apparatus 60 can be moved along the path determined by the first track 31 by means of a power drive device 64 on the other trolley 63. The carrier apparatus 60 includes a device holder 67 and a vertical blade 66 that connects the device holder 67 with the trolley 63 and can be offset at an angle in the upper area, as shown in FIG. 1. The vertical blade 66 in the example shown in FIG. 1 is telescopable and thus forms a vertical steering device for the device holder 67 and the medical devices 69 that are held by the device holder 67 and that make possible a vertical movement of the device holder 67 and medical devices 69 as indicated by a double arrow.

The device holder 67 in the example shown in FIG. 1 is configured as an essentially horizontal carrier plate on which the medical device or devices 69 stand.

One or more power drive devices, not shown in FIG. 1, can be provided and configured to rotate the device holder 67 or the entire carrier apparatus 60 around a vertical axis and/or to move the device holder 67 in the vertical direction.

In addition to the power drive devices 43, 53, 63, shown or not shown and described above, or partly or completely integrated in them, position sensors can be provided to record the position of the trolleys 43, 53, 63 along the path determined by the tracks 31, 33, angle positions and positions in vertical direction of the projection surface 41, of the projector 50 and/or of the device holder 67. These sensors can be coupled with a steering device, described below with reference to FIG. 28. Provided that stepper motors are used in the power drive devices, the corresponding positions or coordinates can be determined alternatively by counting the completed steps.

Figure 28:
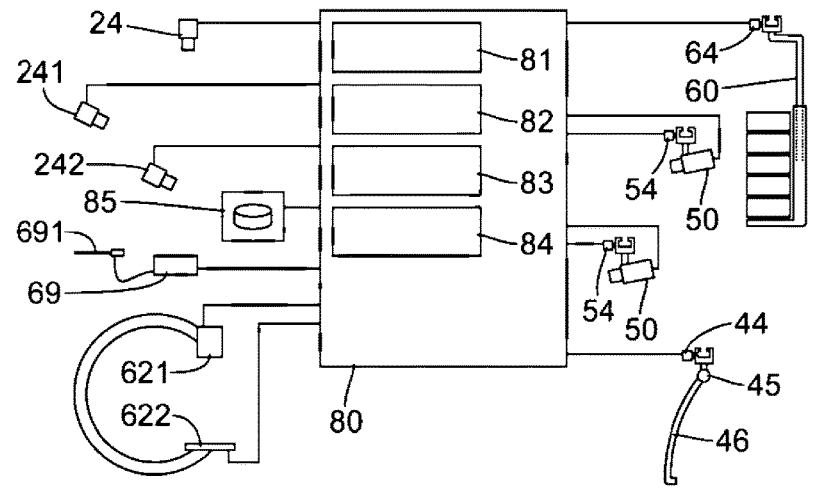
FIG. 28 shows a schematic depiction of a steering device.

The steering device presented below with respect to FIG. 28 can guide the power drive devices on the basis of the recorded positions and optionally in addition on the basis of the position or positions of relevant medical staff or on the basis of gestures of the medical staff recorded by the room camera 24 or other sensors. The steering device can thus provide at all times an arrangement and alignment, which are optimal for medical staff from the ergonometric viewpoint, of the projection surface 41 and of the medical devices 69 carried by the carrier apparatus 60. By dispensing predominantly or—as indicated in FIG. 1—completely with conventional ceiling arms, a vertical laminar flow field 22 becomes possible that is largely or completely free of failures.

Figure 2:
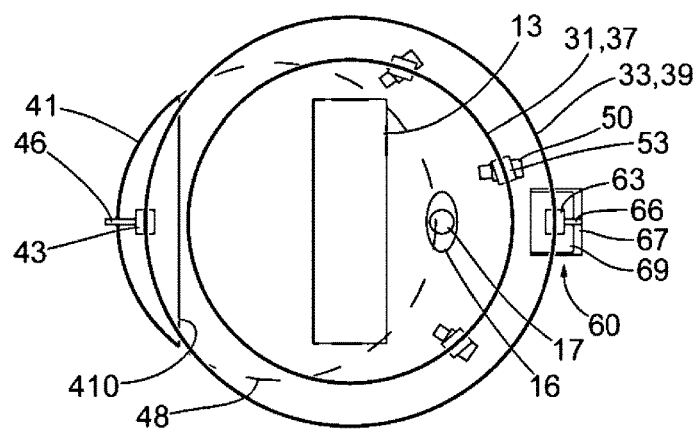
FIG. 2 shows an additional schematic depiction of the medical treatment facility from FIG. 1.

FIG. 2 shows another schematic depiction of the medical treatment facility from FIG. 1. The plane of projection of FIG. 2 is perpendicular to the plane of projection of FIG. 1 and parallel to the floor surface 11 and to the ceiling surface 12 of the medical treatment facility 10. The tracks 31, 33 and the paths 37, 39 determined by the tracks 31, 33 circumscribe in circular manner the area of the ceiling surface that is positioned above the treatment table 13. The trolley 43 along with the projection surface 41, the trolley 53 along with the projector 50, and the trolley 63 along with the carrier apparatus 60 can be moved along the paths 37, 39 determined by the tracks 31, 33. The projection surface 41 and the carrier apparatus 60 are shown in FIG. 2 in the same position as in FIG. 1; the projector 50 is shown in a position that is slightly displaced with respect to the position shown in FIG. 1.

In FIGS. 1 and 2, the contours of the spherical surface on which the projection surface 41 is situated are indicated in broken lines. In the situation illustrated in FIGS. 1 and 2, the head 17 and/or the eyes of the medical staff 16 are approximately on this spherical surface 48. This configuration has shown itself, for example in observing images that are recorded by an endoscope with an image angle of 70 degrees, to be approximately optimal with respect to achieving an immersive, three-dimensional image impression for the medical staff 16.

Contrary to FIG. 1, in FIG. 2 one also sees additional projectors, not labeled with reference numbers, that can be operated in alternation or simultaneously to allow a uniform illumination of the projection surface 41.

Figure 3:
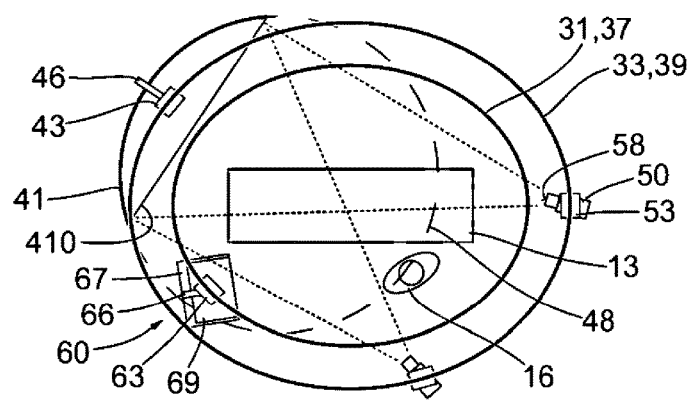
FIG. 3 shows a schematic depiction of an additional medical treatment facility.

FIG. 3 shows a schematic depiction of an additional medical treatment facility, which resembles in some respects the medical treatment space described above with reference to FIGS. 1 and 2. Contrary to the example in FIGS. 1 and 2, in the example in FIG. 3 the tracks 31, 33 and the paths 37, 39 determined by the tracks 31, 33 each have an elliptical shape. An elliptical or oval shape of the paths 37, 39 can be advantageous, for example, under tight space conditions. In the configuration shown in FIG. 3, both the projection devices 50 and the projection screen 41 and carrier apparatus 60 are each rotated with respect to the associated trolleys 53, 43 or 63.

FIGS. 4 through 9 show schematic depictions of various embodiments of ceiling supply systems 23 and in particular of the track devices formed by tracks 31, 32, 33, 34 on the ceiling supply systems 23, as well as of trolleys 43, 53 on the tracks 31, 32, 33, 34. The illustrations each have for the most part the quality of cut-out depictions, where the planes of projection or the illustrated sectional planes correspond to the plane of projection of FIG. 1 and thus are disposed vertically in the medical treatment facility.

In FIGS. 4 through 9, a room illumination 25 is shown in each case, with a light source and an indicated reflector. Structural details of the ceiling supply systems 23 and of the trolleys 43, 53 are each indicated in all cases. Also, the ceiling of the medical treatment space in FIGS. 4 through 9 is indicated in each case only by the ceiling surface 12 and the air nozzles 21 to generate the vertical laminar flow field 22.

Some of the embodiments presented with reference to FIGS. 4 through 9, alternatively, can be integrated in the ceiling of the medical treatment facility provided that the underside of the supply system 23 or the undersides of the tracks 31, 32, 33, 34 are positioned flush with the ceiling surface.

Figure 4:
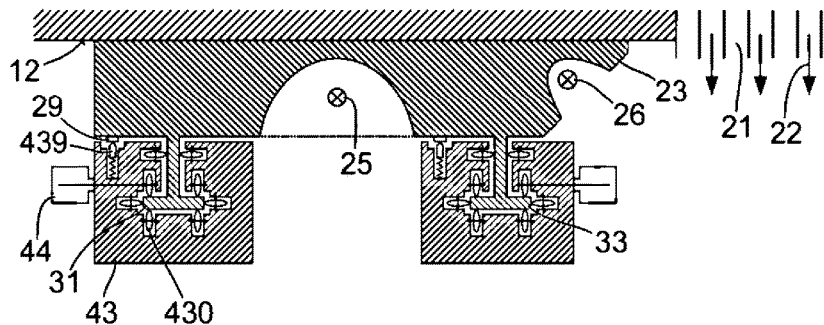
FIG. 4 shows a schematic sectional depiction of a track device.

In the example illustrated in FIG. 4, tracks 31, 33 are foreseen, with one trolley 43 situated on each. The tracks 31, 33 can be situated parallel or essentially parallel to one another, or can be at a constant distance. Alternatively, the tracks 31, 33 can be at a varying distance. Each of the two tracks 31, 33 has a cross-section that corresponds essentially to a "T" rotated by 180 degrees. Each trolley 43 comprises several rollers 430 whose axles are each perpendicular or essentially perpendicular to the local direction of the path 37 or 39 (see FIGS. 2, 3) determined by the track 31 or 33. In each case one or more rollers 430 are positioned over a horizontal running surface on the track 31, 33 that is aligned upward in order to transmit the weight impact of the trolley 43 and the devices affixed to it onto the track 31, 33. In each case one or more rollers 430 are contiguous with lateral or vertical running surfaces or with horizontal running surfaces of the tracks 31, 33 that are aligned downward in order to divert horizontal forces, forces aligned vertically upward, and tipping moments onto the tracks 31, 33. One or more running wheels 430 in each case can be powered by a power drive device 44 in order to move or slide the trolley 43 along the corresponding track 31, 33.

In addition, a contact track 29 of an electrically conductive material is provided parallel to each track 31, 33. A sliding contact 439 is positioned on the trolley 43 in such a way that it is contiguous with the contact track 29 and forms an electrically conductive connection with it. A spiral spring or other elastic element can be provided in order to press the sliding contact 439 against the contact track 29. The sliding contact 439 thus forms a contact device to form an electrically conductive contact with the contact track 29. The contact track 29 and the sliding contact 439 can be provided to transmit electric current and electric signals between the ceiling supply system 23 and the trolley 43. The second pole, required to close a power circuit, is formed for example by the tracks 31, 33. Alternatively or additionally, further contact tracks can be provided, with which other sliding contacts are contiguous.

Besides electric power, it is possible to transmit, in particular, low-frequency signals or signals with low data rates or bandwidths over the contact tracks 29 and the sliding contacts 439. In particular, control signals for the power drive device 44 and, in the opposite direction, position signals, which indicate positions in the corresponding degrees of freedom, are transmitted by means of the contact tracks 29 and the sliding contacts 439. At least when the trolley 43 is not moved, it is possible in addition to transmit signals with higher data rates or bandwidths, for example image signals.

Figure 5:
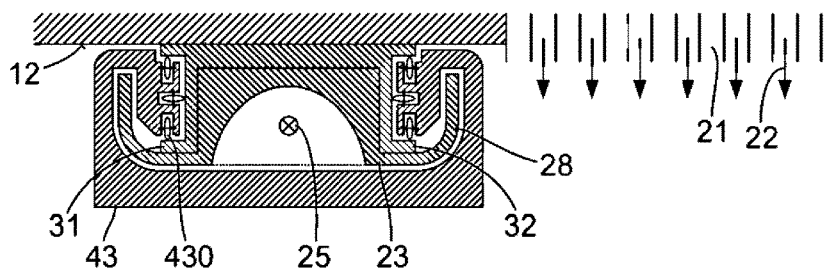
FIG. 5 shows a schematic sectional depiction of an additional track device.

FIG. 5 shows a schematic depiction of an embodiment that in a few respects resembles the embodiment in FIG. 4.

In the embodiment in FIG. 5, the trolley 43 engages in two opposite U-shaped tracks 31, 33 that are turned away from one another and is guided therein with several rollers 430 in each case. The trolley 43 here also grips two diaphragms 28. The diaphragms 28 cover two tracks 31, 33 partly or completely, so that these are not visible to an observer in the medical treatment facility. In addition, the diaphragms 28 can protect the tracks 31, 32 and the rollers 430 on the trolley 43 from contamination and damage and can absorb or repress friction occurring on the tracks 31, 32 and on the rollers 430.

Contrary to FIGS. 4 and 6 through 9, examples of simple structural characteristics of the ceiling supply system are also indicated in FIG. 5. The tracks 31, 32 are components of a profile module that can first be anchored on the ceiling surface 12. Thereafter, the room illumination 25 and the diaphragms 28 in particular can be inserted as a unit into the profile module.

Contact tracks and sliding contacts as in the example in FIG. 4 are not shown in FIG. 5 but can also be provided in the embodiment in FIG. 5.

Figure 6:
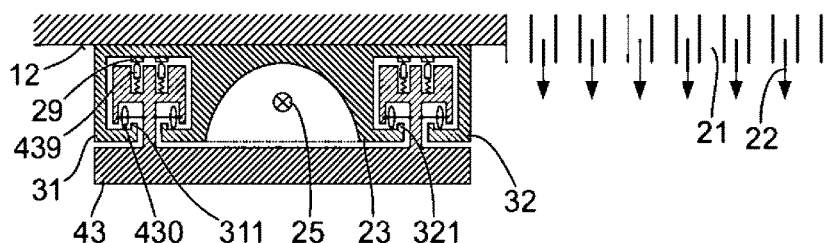
FIG. 6 shows a schematic sectional depiction of an additional track device.

FIG. 6 shows a schematic depiction of an additional embodiment, in which the trolley 43 is guided and held by two tracks 31, 32. Each track 31, 32 comprises a C-shaped cross-section that is open on the underside. Rollers 430 of the trolley 43 are positioned inside the C-shaped cross-sections of the tracks 31, 32 and support themselves there on horizontal or essentially horizontal running surfaces.

To guide the trolley 43 in the horizontal direction perpendicular to the paths determined by the tracks 31, 32, the guide studs 311, 321, for example, which are indicated in FIG. 6 and protrude upward on the edges of a track 31, 32 that are opposite one another, are provided for the rollers 430. As an alternative or in addition, other rollers can be foreseen that are contiguous with the vertical running surfaces in the tracks 31, 32 in order to transmit horizontal forces onto the tracks 31, 32.

In the hollow spaces in the tracks 31, 32 that are open underneath, one or—as indicated in FIG. 6—more contact tracks 29 are positioned in each case. Corresponding sliding contacts 439 are provided on the trolley 43.

Figure 7:
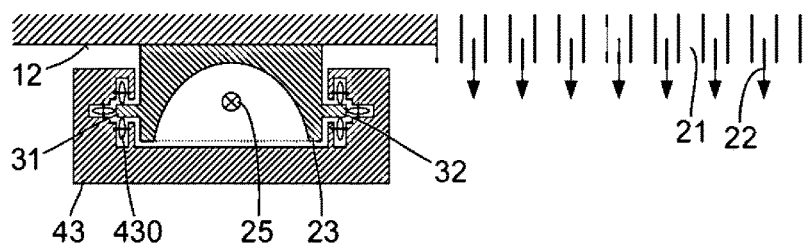
FIG. 7 shows a schematic sectional depiction of an additional track device.

FIG. 7 shows a schematic depiction of an additional embodiment in which two parallel tracks 31, 32 are positioned on sides of the ceiling supply system 23 that face away from one another. Each of the tracks 31, 32 protrudes horizontally in a stud-shaped manner.

The trolley 43 comprises rollers 430 that are contiguous with running surfaces that are horizontal and directed upward, or vertical, or horizontal and directed downward and that make possible a diversion or transmission of forces and moments onto the tracks 31, 32.

Figure 8:
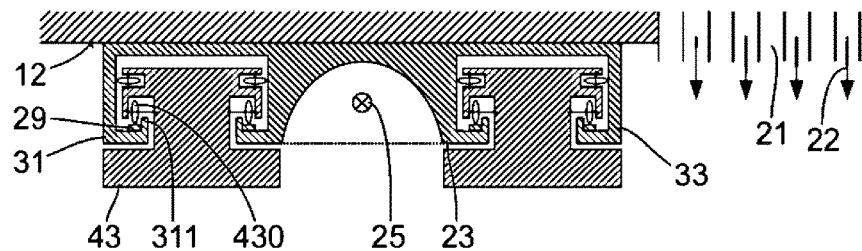
FIG. 8 shows a schematic sectional depiction of an additional track device.

FIG. 8 shows a schematic depiction of an embodiment in which, similarly as in the embodiment in FIG. 4, two trolleys 43 independently of one another are each guided and held by a track 31, 33. The individual tracks 31, 33 and the guidance of the trolleys 43 in the tracks 31, 33 resemble the embodiment in FIG. 6. Contrary to the embodiment in FIG. 6, in the embodiment in FIG. 8, alternatively to the guide studs 311 or—as shown in FIG. 8—in addition to them, rollers 430 are provided that are contiguous with vertical running surfaces in the tracks 31, 33. In addition, contact tracks 29 are provided in the tracks 31, 33 that form running surfaces for one or more guide wheels 430 in each case. Transmission of electric power and/or electric signals to or from the trolley devices 43 is possible via rollers 430 that are contiguous with the contact tracks 29.

Figure 9:
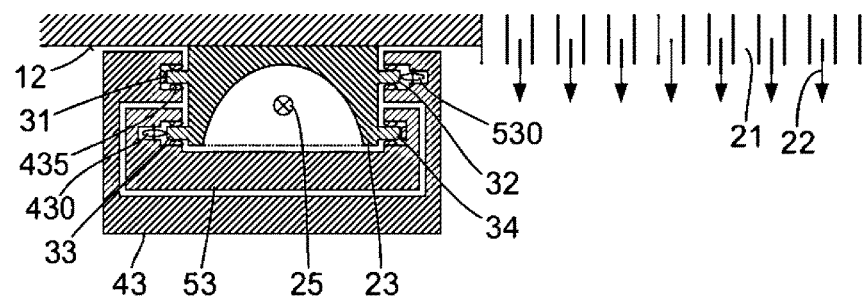
FIG. 9 shows a schematic sectional depiction of an additional track device.

FIG. 9 shows a schematic depiction of an additional embodiment in which, similarly as in the embodiment in FIG. 7, horizontally protruding stud-shaped tracks 31, 32, 33, 34 are provided on sides of the ceiling supply system 23 that are turned away from one another. Contrary to the embodiment in FIG. 7, two pairs of tracks 31, 32 or 33, 34 are provided. A first trolley 43 is held and guided by a first pair of tracks 31, 32. A second trolley 53 is held and guided by a second pair of tracks 33, 34. Owing to a corresponding configuration of the trolleys 43, 53, as is indicated by way of example in FIG. 9, the trolleys 43, 53 can be moved independently of one another along the paths determined by the tracks 31, 32 or 33, 34 without colliding with one another.

Contrary to the embodiments in FIGS. 4 through 8, in the embodiment in FIG. 9, instead of rollers 430, glider bearings 435 are predominantly provided. In addition to the glider bearings, in each case a roller 430, 530 is provided that can be powered by a power drive device, not shown in FIG. 9, in order to move the associated trolley 43, 53.

In the embodiments in FIGS. 4 through 8, the rollers 430 can be partly or completely replaced by glider bearings 435, as described above with reference to FIG. 9. In the embodiment in FIG. 9, the glider bearings 435 can be partly or completely replaced by rollers. In particular, in each of the embodiments presented with reference to FIGS. 4 through 9, it is possible to provide rollers to absorb weight impacts, and glider bearings for horizontal guidance and to absorb other forces and moments. It can be advantageous in each case to provide a powered running wheel to move the trolley. To make possible a power drive without slippage, a power-drive running wheel can be configured as a toothed wheel and an opposite running surface as a gear rack. Alternatively to a form-locked or force-locked roller acting reciprocally with the associated running surface, it is also possible to use an electromagnetic linear drive, an ultrasound motor, a drive via rope pull or manual mobility.

The rollers or glider bearings of the embodiments in FIGS. 4 through 9 can be replaced partly or completely by devices for magnetic hoisting and guidance of the trolleys 43. For this purpose, permanent magnets and/or electromagnets and devices for controlling constant distances are provided. Devices for magnetic hoisting and guidance of the trolleys 43 can, in addition, be configured to power the trolleys magnetically.

In FIGS. 4 through 9, reference number 43 has been used by way of example for the trolleys, and in FIG. 9 reference number 53 is also used. Reference numbers 43, 53 refer in FIGS. 1 through 3 to the trolleys that are associated with projection surfaces 41 or projectors 50. The trolleys shown in FIGS. 4 through 9, however, can also be associated with the carrier apparatus 60 from FIGS. 1 through 3 or can carry other devices, in particular also the devices presented hereinafter with reference to FIGS. 10 through 24.

Figure 10:
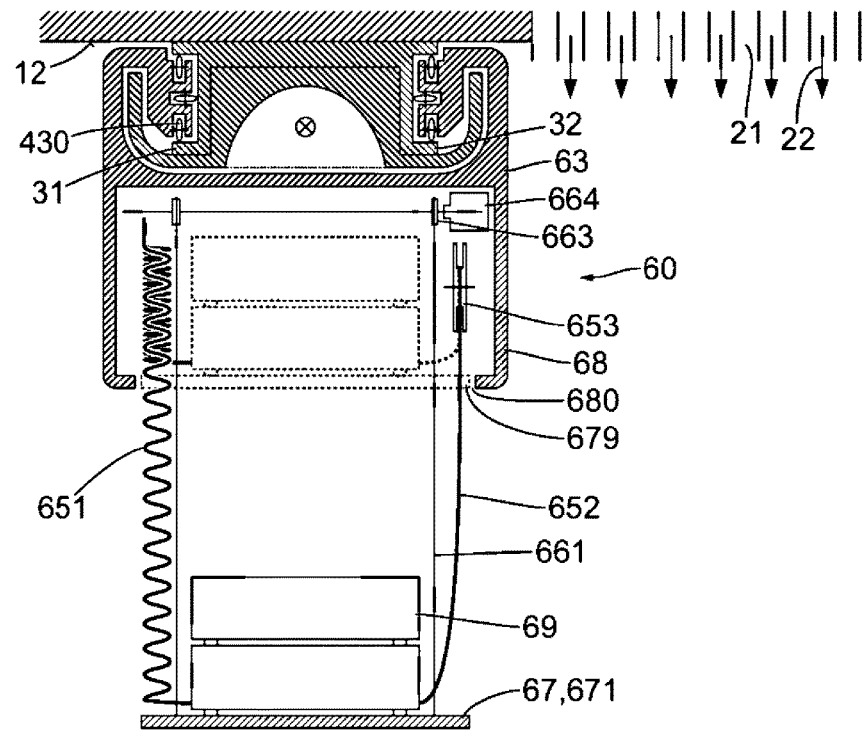
FIG. 10 shows a schematic depiction of a carrier apparatus.

FIG. 10 shows a schematic depiction of an additional carrier apparatus 60 with a configuration that is an alternative to the one shown in FIGS. 1 through 3. The depiction in FIG. 10 has to some extent the character of a sectional depiction, such that the plane of projection corresponds to those in FIGS. 1 and 4 through 9.

The trolley 63 is connected with a container 68 or—as indicated in FIG. 10—is of one-piece configuration. There is an opening 680 on the underside of the container 68. The device holder 67 in this embodiment is not guided on a vertical telescopable blade, but rather suspended on several ropes 661, whose upper ends can be wound up on reels 663. The reels 663 can be powered by an electromotor 664 in order to wind or unwind the ropes 661 and thus to move the device holder 67 vertically upward or downward. Thus the ropes 661, the reels 662 and the electromotor 664 form a lifting device for the device holder 67.

The device holder 67 is depicted with two medical devices 69 in a lower position or operating position 671 in broken lines in FIG. 10. The device holder 67, in addition, is depicted together with the medical devices 69 in broken lines in a higher resting position 679. In the resting position 679 the device holder 67 closes the opening 680 on the underside of the container 68. The devices 69 are positioned in the hollow space configured by the container 68 and there largely protected from contamination and damage. Owing to an optically quiet configuration of the outside of the container 68 and of the underside of the device holder 67, a calm optical impression emerges that is not likely to distract medical staff from their task and that can enhance concentration on relevant information sources.

Many medical devices 69 are dependent on a supply of electrical power, illuminating light from a high-voltage light source, compressed air or other fluids, as well as on an exchange of electrical or optical signals (for example via a Storz Communication Bus SCB) with other devices. To make possible a start-up and turn-off of the devices 69 without previous establishment or interruption of current connections, the medical devices 69 can remain constantly connected with power, signal, light and fluid sources, both in the operating position 671 and in the resting position 679 and in all positions in between.

For this purpose, as an alternative or simultaneously, one or more extensible cables 651 and/or one or more coilable cables 652 are provided between the interior of the container 68 and the device holder 67 or the medical devices 69 positioned on the device holder 67. The extensible cable 651 has, in particular, a helical shape, similar to a cable generally called a spiral cable, as is provided conventionally between a telephone and the user. The coilable cable 652 can be rolled up on a reel 653. The reel 653 can be powered mechanically or by a spring in order to roll up the coilable cable 652 by self-actuation when the device holder 67 with the medical devices 69 is raised from the operating position 671 into the resting position 679.

FIG. 11 shows a schematic depiction of an embodiment of a carrier apparatus 60 that is an alternative to the embodiment in FIG. 10. The embodiment shown in FIG. 11 resembles the embodiment presented above with reference to FIG. 10 in a few characteristics. What particularly distinguishes the embodiment in FIG. 11 from the one in FIG. 10 is that instead of several ropes 661, a scissors mechanism 667 is provided. The scissors mechanism 667, contrary to the cables of the embodiment in FIG. 10, makes possible a rigid guidance of the device holder 67, aside from the residual elasticity that is proper to it. The device holder 67 is not only kept at all times in the horizontal position by the scissors mechanism—as also by the cables of the embodiment in FIG. 10. The scissors mechanism 667, in addition, can also transmit onto the trolley 63 the horizontal forces exerted on the device holder 67. Thus the scissors mechanism 667 has the function of a steering device for largely rigid guidance along a predetermined straight vertical course.

In addition, the scissors mechanism 667 can be used to move the device holder 67. A force that, for example, impacts only on the topmost pair of blades of the scissors mechanism 667 leads to a uniform reshaping of the entire scissors mechanism 667. To that extent, the scissors mechanism 667 also has the function of a lifting device for the device holder 67.

Alternatively, the cables of the embodiment in FIG. 10 can be combined with the scissors mechanism 667 of the embodiment in FIG. 11. In this case, the scissors mechanism 667 acts primarily as a largely rigid guide for the device holder 67, which can accept horizontal forces and transmit them to the trolley 63, while the cables act as lifting devices for raising (and lowering) the device holder 67.

Contrary to FIG. 10, in FIG. 11 no cables are illustrated for transmitting electric power, electrical or optical signals, illuminating light or fluids between the container 68 and the device holder 67 and/or medical devices 69 onto the device holder 67. Cables can be foreseen as they were presented above with reference to FIG. 10. Alternatively, cables can run along the blades of the scissors mechanism 667 or can be affixed on them (in particular, at specific points).

FIG. 12 shows a schematic depiction of a carrier apparatus 60, as it is presented above with reference to FIGS. 10 and 11, with a supply arm 71. The device holder 67 can be guided and raised corresponding to one of the embodiments discussed above with reference to FIGS. 10 and 11 or in other manner. Corresponding characteristics are therefore not shown in FIG. 12.

The supply arm 71 is connected at its radially inner end with the ceiling of the medical treatment facility via a joint 72, where the joint 72 makes it possible for the supply arm 71 to pivot around a vertical axis. The radially outer end 73 of the supply arm 71 extends through a lateral opening 687 into the container 68 and is fed there in one or more guide tracks 74. The guide tracks 74 make possible, in particular with a non-circular shape of the path determined by the tracks of the ceiling supply device, a length compensation or a compensation for a variation in the distance between the joint 72 and the container 68.

The radially outer end 73 of the supply arm 71 is connected with the upper end of the helical, extensible cable 651 described above with reference to FIG. 10, in particular by means of an elastic cable 75. In particular, the extensible cable 651 and the elastic cable 75 are formed by different portions of the same cable, which is configured as one piece. The elastic cable 75 makes it possible to slide the radially outer end 73 of the supply arm 71 in the container 68, in particular because of a slack loop, as indicated in FIG. 12, with variable geometric shape.

The supply arm 71, the elastic cable 75 and the extensible cable 651 are configured, in particular, to convey one or more different fluids to or from one of the devices 69 on the device holder 67. Therefore the joint 72, in particular, comprises an insulation by means of one or more shaft seals (often referred to as oil seals) or other insulations. Alternatively or in addition, the supply arm 71, the elastic cable 75 and the extensible cable 651 are configured to conduct electric current, electrical or optical signals or illuminating light. For this purpose, one or more corresponding cables can each be positioned on or—advantageously, as a rule—in the supply arm.

The supply arm is not configured to receive forces that exceed its own weight. The cross-section of the supply arm 71 can therefore be small and configured for a minimal disturbance of the vertical laminar flow field 22, for example by a tear-drop shape. A supply arm with the aforementioned properties can also be used with other carrier apparatuses than the one described with reference to FIGS. 10 through 12, for example with the one presented with reference to FIGS. 1 through 3. In addition, a supply arm 71 with the properties described here can be used to conduct electric power and electrical or optical signals to a projector, to a projection surface or to another display device or to one of the apparatuses described below with reference to FIGS. 13 and 14.

Also shown in FIG. 12 is a delivery arm 761 with several blades 762, which are connected by joints 763 with one another and jointedly connected with the device holder 67. The delivery arm 761 bears a satellite device 768 on its end that is remote from the device holder 67. On or in the delivery arm 761, one or more cables 765 can be mounted to transmit electric power, electrical or optical signals, illuminating light (for example, for endoscopes) and fluids. The cable or cables 765 couple one or more devices 69 on the device holder 67 with the satellite device 768. The satellite device 768 can provide operator controls or a user interface in order to control or monitor functions of one or more medical devices 69 on the device holder 67. In addition, the satellite device 768 can comprise one or more connections 769 on which, for example, illuminating light generated by one of the medical devices 69 is provided.

Because the delivery arm 761 is configured with one or more joints 763, the satellite device 768 can be positioned by medical staff in ergonomically optimal manner.

Contrary to the depiction in FIG. 12, the delivery arm 761, instead of with the device holder 67, can alternatively be jointedly mechanically connected with the container 68, with the supply arm 71, with the joint 72 of the supply arm 71, close to the joint 72 of the supply arm 71 with the ceiling of the medical treatment space 10 or with another attachment point. In the case of a mechanical attachment of the delivery arm 761 on the joint 72 of the supply arm 71, the delivery arm 761 can be rotatable or pivotable together with the supply arm 71 or independently of it. In the case of a mechanical attachment of the delivery arm 761 on the supply arm 71, the supply arm 71, unlike as described above, is configured as a girder for receiving or transmitting or diverting mechanical forces and moments.

The delivery arm 761 can be connected, merely in jointed, mechanical manner, with the device holder 67, with the container 68, with the supply arm 71, with the joint 72 of the supply arm 71, with the ceiling of the medical treatment facility 10 or with another attachment point. Alternatively, one or more linear translational degrees of freedom can be foreseen that, in particular, make possible a translation of the end of the delivery arm 761 that is at a distance from the satellite device 768 in the horizontal and/or vertical direction. For example, one or more steering devices can be provided that each make it possible to slide the end of the delivery arm that is at a distance from the satellite device 768 along a straight or curved path. In particular, the end of the delivery arm 761 that is at a distance from the satellite device 768 can be slidable along the supply arm 71.

Figure 13:
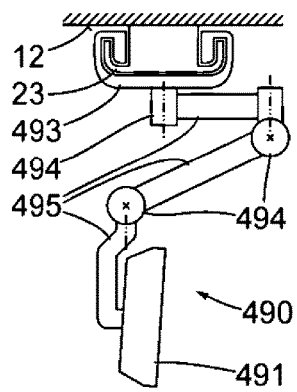
FIG. 13 shows a schematic depiction of a display device.

FIG. 13 shows a schematic depiction of a display device 490 that is distinguished from the display device that is formed by the projection surface 41 and projector 50, which are presented above with reference to FIGS. 1 through 3. A screen 491 is mechanically connected via several joints 494 and blades 495 with a trolley 493. The trolley can comprise characteristics of the trolley presented above with reference to FIGS. 4 through 9 and makes possible a movement along a ceiling supply system 23 on a ceiling surface 12. In the illustrated example, a blade 495 can pivot only in a horizontal plane or around a vertical axis, while another blade 495 can pivot around a vertical axis and around a horizontal axis.

Figure 14:
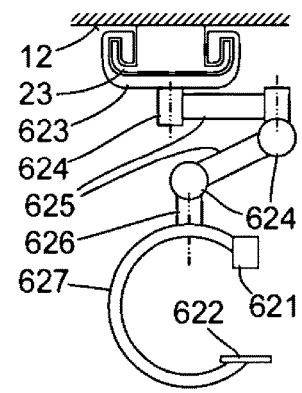
FIG. 14 shows a schematic depiction of an additional carrier apparatus.

FIG. 14 shows a schematic depiction of a carrier apparatus for carrying an x-ray source 621 and a locally sensitive x-ray detector 622 and/or an image sensor sensitive to x-ray radiation. The x-ray source 621 and x-ray detector 622 are rigidly interconnected via a C-shaped arc 627. The C-shaped arc 627 is connected with a trolley 623 by several joints 624 and several blades 625, 626. The trolley 623 comprises, in particular, characteristics that are described above with reference to FIGS. 4 through 9. The trolley 623 makes possible a movement along the path determined by tracks on the ceiling supply system 23 parallel to the ceiling surface 12.

In the embodiments in FIGS. 13 and 14, the blades 495 and joints 494 or the blades 625 and joints 624 constitute carrier apparatuses for the screen 491 or for the x-ray source 621 and x-ray detector 622. Because of the maneuverability by means of trolleys 493 or 623, the blades 495, 625 can be essentially shorter than conventional ones and thus disturb a vertical laminar flow field to a lesser degree than do conventional girders. In addition, the blades 495 and 625 can be positioned entirely outside the vertical laminar flow field, at least when not in use or when the screen 491 or x-ray source 621 and x-ray detector 622 are in resting position.

Figure 15:
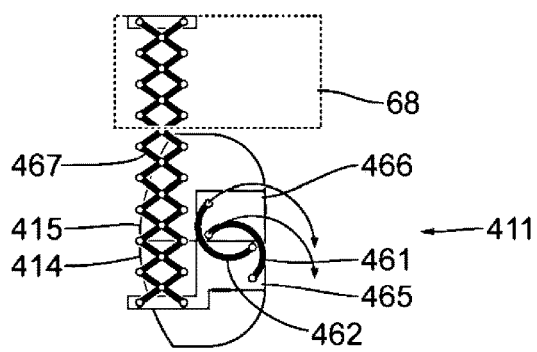
FIG. 15 shows a schematic depiction of a projection surface.
Figure 16:
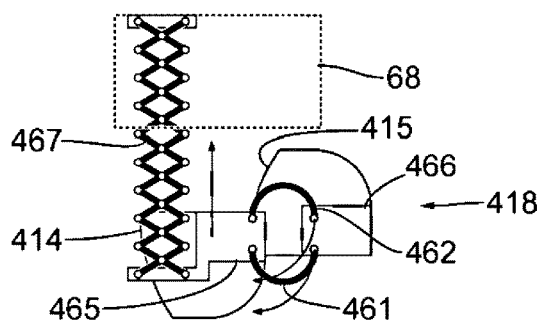
FIG. 16 shows an additional schematic depiction of the projection surface from FIG. 15.
Figure 17:
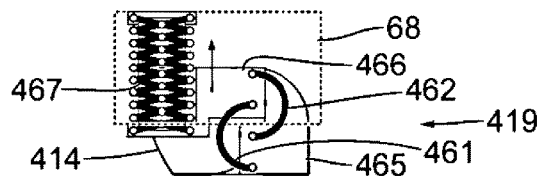
FIG. 17 shows an additional schematic depiction of the projection surface from FIGS. 15 and 16.

FIGS. 15 through 17 show schematic depictions of a projection surface 41 in an operating condition 411 (FIG. 15) and two additional conditions 418, 419. The planes of projection of FIGS. 15, 16 and 17 correspond to the planes of projection of FIGS. 1 and 4 through 14 or intersect them in a vertical straight line. Similarly as in the carrier apparatus presented above with reference to FIG. 11, a container 68 and a scissors mechanism 467 are foreseen. Instead of a device holder, a projection surface is foreseen that includes two areas 414, 415 and that can be vertically transported or moved by means of a scissors mechanism 467. The projection surface 414, 415 is domed and curved or comprises a positive Gaussian curvature. In particular, the projection surface 414, 415 has the shape of a portion of a spherical surface. The depictions in FIGS. 15 through 17 show the projection surface 414, 415 from the side, that is, a connecting line between a center point of the projection surface 414, 415 and a curvature center point of the projection surface 414, 415 is parallel to the planes of projection of FIGS. 15 through 17 and runs horizontally from left to right.

On the side turned toward the observer, every area 414, 415 of the projection surface is rigidly connected with a plate 465, 466. The plate 465 on the first area 414 of the projection surface and the plate 466 on the second area 415 of the projection surface are jointedly connected with one another via two connecting rods 461, 462. The connecting rods 461, 462 in the example illustrated in FIGS. 15 through 17 are each arch-shaped, in particular in the shape of a half arc. Corresponding plates and connecting rods are positioned on the sides of the areas 414, 415 of the projection surface that are not visible in FIGS. 15 through 17 and are turned away from the observer.

The mechanical coupling of the areas 414, 415 of the projection surface by the connecting rods 461, 462 makes possible essentially only a movement of the areas 414, 415 of the projection surface relative to one another, in which both areas do not modify their relative orientation.

In particular, the areas 414, 415 of the projection surface can be converted from the operating condition 411 shown in FIG. 15 by a movement that is indicated in FIG. 15 by arc-shaped arrows, into the condition shown in FIG. 16 and from there into the resting position shown in FIG. 17 by a movement that is indicated by arc-shaped arrows in FIG. 16. It can be recognized that the vertical extension of the projection surface 414, 415 in the resting position 419 is only half as large as in the operating condition 411.

After the transformation from operating condition 411 into resting condition 419 or simultaneously, the projection surface 414, 415 can be moved into the housing 68 indicated in broken lines by means of the scissors mechanism 467. In the housing 68, the projection surface 414, 415 can be protected from contamination and damage, particularly if, contrary to the depiction in FIGS. 15 through 17, a cap or cover closes the opening on the underside of the housing 68. Because of the transformation or conversion of the projection surface 414, 415 into resting position 419, the housing 68 can be markedly smaller than it would have to be if it were required to incorporate the projection surface 414, 415 in the operating condition 411. A cap or covering can be connected with the housing 68, in particular with the edge of the opening in the housing 68, by means of a joint. Alternatively, a cap or covering is positioned rigidly on the first portion 414 of the projection surface so that the opening in the housing 68 is closed when the projection surface in its resting condition has completely entered the housing 68.

Figure 18:
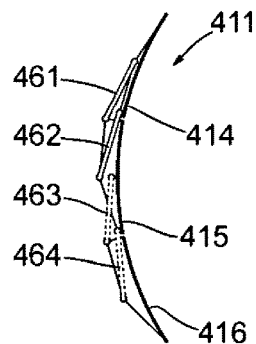
FIG. 18 shows a schematic depiction of an additional projection surface.
Figure 19:
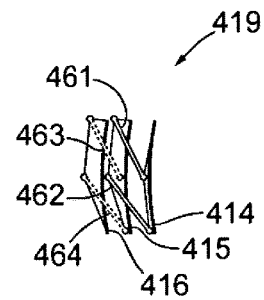
FIG. 19 shows an additional schematic depiction of the projection surface from FIG. 18.

FIGS. 18 and 19 show schematic depictions of an additional reshapable projection surface in an operating condition 411 (FIG. 18) and in a resting position 419 (FIG. 19). The planes of projection of FIGS. 18, 19 correspond in particular to the planes of projection of FIGS. 1 and 4 through 17. A corresponding transformation, however, is also a possible alternative in the horizontal direction, where horizontal planes of projection would yield corresponding images.

The projection surface comprises several areas 414, 415, 416 and has a dome-shaped, especially spherical, curvature. The areas 414, 415, 416 of the projection surface are jointedly connected with one another by connecting rods 461, 462, 463, 464. The distance of the joints between the first connecting rod 461 or the second connecting rod 462 and the first area 414 of the projection surface is smaller than the distance of the joints between the first connecting rod 461 or the second connecting rod 462 and the second area 415 of the projection surface. Alternatively or in addition, the connecting rods 461, 462 have different lengths between the joints. The same holds true for the second area 415 of the projection surface and the third area 416 of the projection surface as well as the third connecting rod 463 and the fourth connecting rod 464. As a result, the connecting rods and the joints form no parallelograms at the areas 414, 415, 416 of the projection surface. As is recognizable in a comparison of the operating condition 411 shown in FIG. 18 and the resting condition 419 shown in FIG. 19, this causes a non-parallel sliding of the areas 414, 415, 416 of the projection surface. While the areas 414, 415, 416 of the projection surface, corresponding to the curvature of the projection surface, have different orientations in the operating condition 411, in the resting condition 419 they are positioned essentially parallel to one another. This can make possible a tighter gripping of the projection surface or of its areas 414, 415, 416.

When the projection surface 414, 415, 416, similarly as with the embodiment in FIGS. 15 through 17, is to be stowed in a container in its resting condition 419 shown in FIG. 19, the parallelism of the areas 414, 415, 416 of the projection surface, recognizable in FIG. 19 can allow smaller dimensions for the container.

With a reshaping of the projection surface between its operating condition 411 and its resting condition 419, or with the corresponding sliding of the areas 414, 415, 416 in relation to one another, the connecting rod 462 bypasses the joint between the connecting rod 463 and the second area 415 of the projection surface. In addition, the connecting rod 463 bypasses the joint between the connecting rod 462 and the second area 415 of the projection surface. This is possible if the connecting rod 462 and its joint to the second area 415 of the projection surface on the one hand, and the connecting rod 463 and its joint to the second area 415 of the projection surface on the other hand, are not situated in one plane.

The depiction of the connecting rod 462 in shaded lines and of the connecting rod 463 in broken lines indicates that the connecting rods 462, 463 are not situated in one plane. For example, the plane in which the connecting rod 462 (and also, in particular, the connecting rod 461) can pivot and the plane in which the connecting rod 463 (and also, in particular, the connecting rod 464) can pivot are parallel to and at a distance from one another. More generally, the connecting rods 462, 463 must be disposed and formed in such a way that they do not block one another.

For this purpose, the connecting rods 462, 463 can be positioned in two different planes or, more generally, can be positioned and configured in such a way that the level or curved surfaces that they pass over do not intersect. Alternatively, the connecting rods 462, 463 can each be of arched configuration and positioned, for example, inside the same plane, similarly as with the example presented above with reference to FIGS. 15 through 17.

Figure 20:
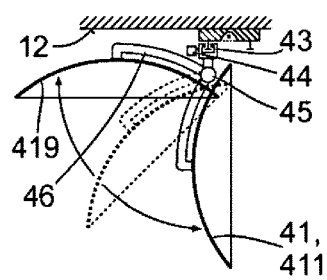
FIG. 20 shows a schematic depiction of an additional projection surface.

FIG. 20 shows a schematic depiction of a second embodiment of a projection surface 411 that resembles in some respects the projection surface presented above with reference to FIGS. 1 through 3. The plane of projection of FIG. 21 corresponds in particular to the plane of projection of FIGS. 1 through 3. The projection surface 411, similarly as presented above with reference to FIGS. 1 through 3, is movably attached to a track 31 by means of a trolley 43.

Contrary to the embodiment presented above with reference to FIGS. 1 through 3, a joint 45 is provided between the trolley 43 and the projection surface 41, in particular in the carrier 46. The joint 45 allows the projection surface 41 to pivot around a horizontal axis corresponding to the arched arrows that can be recognized in FIG. 2 between an operating condition 411 and a resting condition 419. In the resting condition 419, the projection surface 41 is situated immediately under the ceiling surface 12, where it does not restrict medical staff and its freedom of movement or does so less than in the operating condition.

Figure 21:
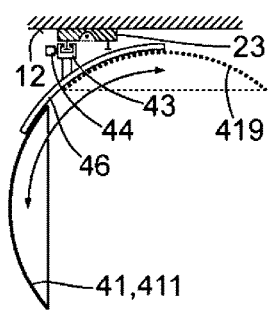
FIG. 21 shows a schematic depiction of an additional projection surface.

FIG. 21 shows a schematic depiction of an additional projection surface 41, which resembles in some respects the embodiment presented above with reference to FIGS. 1 through 3 and 20. The plane of projection of FIG. 21 corresponds in particular to the planes of projection of FIGS. 1 through 3 and 20.

Contrary to the embodiments in FIGS. 1 through 3 and 20, the projection surface 41 can slide along the carrier 46 configured as a curved track or linear guide. Because of the curvature of the projection surface 41 and the corresponding arch-shaped curvature of the carrier 46, the projection surface 41, guided by the carrier 46, can be slid or moved between an operating condition 411 and a resting condition 419 below the ceiling surface 12, corresponding to the arched arrow shown in FIG. 21. In this sliding of the projection surface 41, it is pivoted simultaneously around a horizontal axis.

Similarly as with the embodiment in FIG. 20, the projection surface 41 in the resting condition 419 below the ceiling surface 12 constitutes no obstacle or disturbance or restriction for medical staff and its freedom of movement. If the ceiling supply system 23 and thus the track of the ceiling supply system 23 that guides the trolley 43 is sufficiently far removed from the vertical laminar flow field 21 (see FIG. 1) that is not shown in FIG. 21, the projection surface 41 even in its resting condition 419 constitutes no disturbance for the vertical laminar flow field 21.

Figure 22:
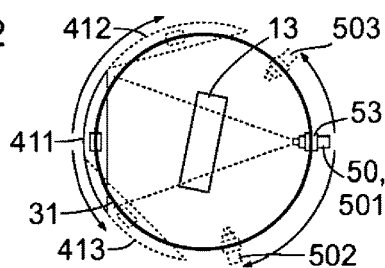
FIG. 22 shows an additional schematic depiction of the projection surface from FIGS. 20 and 21.

FIG. 22 shows an additional schematic depiction of a projection surface as is described above with reference to FIGS. 1 through 3, 20 and 21. The plane of projection of FIG. 22 corresponds in particular to the planes of projection of FIGS. 2 and 3. The projection surface 41 in its operating condition can be slid along the path determined by the circular track 31 between different operating positions 411, 412, 413. Thus, simultaneously, the projector 50 that can likewise be slid along the path determined by the track in the projection surface 41 can be brought into diametrically opposite working positions 501, 502, 503. In particular, at least either the projection surface 41 depending on the position of the projector 50, or the projector 50 depending on the position of the projection surface, is moved by means of power drive devices and guided by a control device in such a way that they are nearly diametrically opposite one another at all times.

Figure 23:
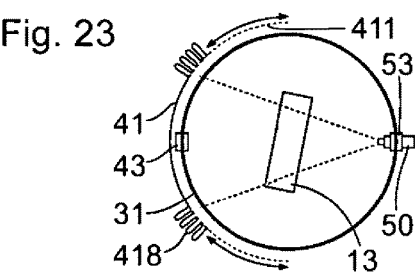
FIG. 23 shows a schematic depiction of an additional projection surface.

FIG. 23 shows a schematic depiction of an additional embodiment of a projection surface 41. The plane of projection of FIG. 22 corresponds in particular to the planes of projection of FIGS. 2, 3 and 22. The projection surface 41 and a projector 50 can be slid or moved by means of trolleys 43 or 53 along a path determined by a track, similarly as described above with reference to FIGS. 1 through 3 and 22. With the embodiment of FIG. 23, the projection surface 41 has the form of a segment of a cylinder in its operating condition, indicated only in dotted lines in FIG. 23. The axis of the cylinder is vertical or perpendicular to the plane of projection of FIG. 23, to the floor surface and to the ceiling surface of the medical treatment facility. The projection surface 41 can be folded together similarly as a curtain. In particular, the projection surface, from its lateral edges, corresponding to the arrows indicated in FIG. 23, can be shifted into an intermediate condition 418 depicted in a wavy line in FIG. 23 and further into a completely folded-together resting condition, which is not shown in FIG. 23. In the resting condition the projection surface 41 constitutes just a narrow bundle, which in addition can be folded away upward to the ceiling surface in order to avoid any impeding of medical staff and their freedom of movement. The projection surface 41 can be stabilized by vertical blades whose upper ends, for example, can be slid in a circular pattern on the track 31 or on a separate track that is attached to the trolley 43.

Figure 24:
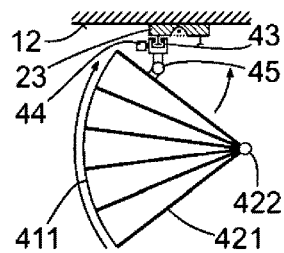
FIG. 24 shows a schematic depiction of an additional projection surface.
Figure 25:
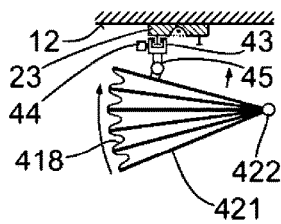
FIG. 25 shows an additional schematic depiction of the projection surface from FIG. 24.

FIGS. 24 and 25 show schematic depictions of an additional embodiment of a projection surface 41 in an operating condition 411 (FIG. 24) and in an intermediate condition 418 (FIG. 24) between the operating condition 411 and a resting condition that is not shown. The planes of projections of FIGS. 24 and 25 correspond, in particular, to the planes of projection of FIGS. 1, 4 through 9, 20 and 21. The projection surface 41, similarly as in the embodiments in FIGS. 1 through 3, 20 and 21, is movably attached by means of a trolley 43 to a track 31 of a ceiling supply system 23 parallel to a ceiling surface 12. Contrary to the embodiments in FIGS. 1 through 3, 20 and 21, the projection surface 41 is constituted by a surface of an elastic membrane, which can be tensed by blades 421 or brought into a predetermined shape. Each of the blades 421 is arched in shape, in particular in semi-circular shape. The ends of the blades 421 are brought together in two joints 422 opposite one another.

In the operating condition 411 of the projection surface 41, shown in FIG. 24, the projection surface between two neighboring blades 421 comprises approximately the shape of a cylinder in each case. Altogether the projection surface 41 thus has nearly the shape of a portion of a spherical surface.

On the basis of the operating condition 411 of the projection surface 41, shown in FIG. 24, the blades can be folded up corresponding to the arrow shown at the left in FIG. 24 and can be pivoted upward corresponding to the arrow shown to the right in FIG. 24. By way of the intermediate condition 418 shown in FIG. 25, the projection surface can be shifted or transformed or reshaped into a resting condition, not shown. In this resting condition the projection surface 41 forms a narrow, arc-shaped bundle that is positioned below the ceiling surface 12. In this resting condition, which is not illustrated here, the projection surface only occupies a small space and constitutes no restriction for the medical staff and their freedom of movement.

Figure 26:
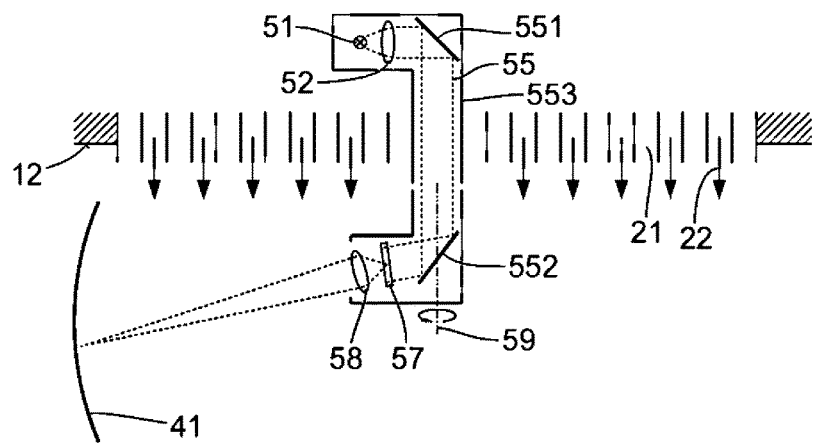
FIG. 26 shows a schematic depiction of a projection system.

FIG. 26 shows a schematic depiction of a projection system as an alternative to the projectors shown in FIGS. 1 through 3, 22 and 23. The plane of projection of FIG. 26 is, in particular, parallel to the planes of projection of FIG. 1. The projection system shown in FIG. 26 can be positioned in the center of the area of the ceiling surface occupied by the air nozzles 21 and, in particular, in the center of a circle, ellipse or oval that is formed by a ceiling supply system or one or more tracks parallel to the ceiling surface 12. As a result of this arrangement, during a movement of a projection surface along a path determined by the track, the projection system is not required to be slid but only rotated around a vertical axis 59. In order to disturb a vertical laminar flow field 22 as little as possible, the projection system is positioned at least partly above the ceiling surface 12.

The projection system includes in particular a light source 51, a collimator 52 and a first mirror 551 that are disposed above the ceiling surface 12, and a second mirror 552, a light modulator 57 and an imaging device 58 that are disposed below the ceiling surface 12. The imaging device 58 is, in particular, a lens, an object lens or a mirror system that has imaging properties. The collimator 52 collimates the light generated by the light source 51. The prevailingly parallel light is directed by the two mirrors 551, 552 onto the light modulator 57. The light modulator 57 is, for example, an LCD component. The image generated by the light modulator 57 is imaged by the imaging device 58 onto a projection surface 41. The collimator 52 and the mirrors 551, 552 as well as a tube 553 between these two define the cross-section of a beam path 55 to transmit or guide light of the light source 51 to the light modulator 57.

By rotating the second mirror 552, light modulator 57 and imaging device 58 around a vertical pivot axis 59, the direction in which an image is projected can be adjusted to the site of the projection surface 41. By tipping and sliding the light modulator 57, imaging device 58 and second mirror 552 as well as individual components not shown in FIG. 26 (in particular, lenses and lens groups) of the imaging device 58, it becomes possible to adjust the projection direction as well as the position and the spatial shape of the image generated by the imaging device 58 to the site, the orientation and the shape of the projection surface 41. In addition, the image of the light modulator 57 generated by the imaging device 58 can be reshaped by sliding and tipping the light modulator 57 and imaging device 58, depending on the position of an observer, in such a way that the observer perceives the image on the projection surface 41 without distortion, in particular parallel straight lines in the image as parallel and right angles as right angles.

Contrary to the depiction in FIG. 26, the light modulator 57 or the light modulator 57 and at least a part of the imaging device 58 can be disposed above the ceiling surface 12. Thereby, the measuring of the components of the projection system disposed below the ceiling surface 12 and the resulting disturbances of the vertical laminar flow field 22 can be further reduced.

IF the light modulator 57 and the imaging device 58, otherwise than as shown in FIG. 26, cannot pivot together around the vertical pivot axis 59, a rotation of the imaging device 58 around the vertical pivot axis 59 can cause a tipping of the projected image. This is especially true when the light modulator 57 is disposed in stationary manner above the ceiling surface 12. In compensation, it is possible to foresee a rotation of the light modulator around the local optical axis of the projection system, and in particular around its surface normal, simultaneously with the rotation of the imaging device 58 around the vertical pivot axis 59. Also possible is a corresponding mechanical coupling between the imaging device 58 and the light modulator 57 or a corresponding logical coupling with a mechanical control device that couples both movements.

As an alternative, between the fixed light modulator 57 and the imaging device 58 that can pivot around the vertical pivot axis 59, it is possible to provide a device for erecting an image, for example an arrangement of one or more prisms. This device to erect the image is rotated by a mechanical or logical coupling simultaneously with a pivoting of the imaging device 58 around the vertical pivot axis 59, in such a way that the angle speeds stand in a fixed ratio to one another.

Alternatively, the projection system or a device controlling the light modulator 57 can be configured in order to rotate the modulation pattern appearing on the light modulator 57, corresponding to a pivot movement of the imaging device 58, around the vertical pivot axis 59.

Figure 27:
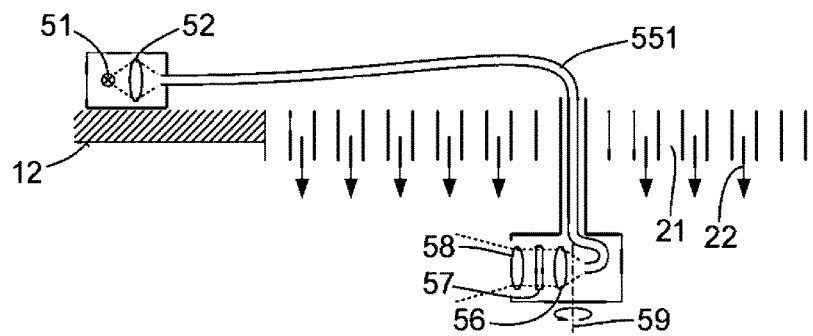
FIG. 27 shows a schematic depiction of an additional projection system.

FIG. 27 shows a schematic depiction of an additional projection system. The plane of projection of FIG. 27 corresponds to the plane of projection of FIG. 26. An imaging device 58, similarly as with the embodiment of FIG. 26, is disposed below the ceiling surface 12, and a light source 51 is disposed above the ceiling surface 12. Light from the light source 51, however, is not transmitted by means of mirrors but rather by means of a light conductor cable 557 from the light source 51 over the ceiling surface 12 to a light modulator 57 and to the imaging device 58. To switch the light generated by the light source 51 into the light conductor cable 557, a converging lens 52 is provided. The light switched out of the light conductor cable 557 is collimated by a collimator 56 and then modulated by the light modulator 57. The light modulator is imaged by the imaging device 58 onto a projection surface that is not shown in FIG. 27.

Similarly as presented above with reference to FIG. 26, it is possible to adjust the projection direction, the position and the shape of the projection surface by rotating the collimator 56, the light modulator 57 and the imaging device 58 around a vertical pivot axis 59 and pivoting around a horizontal axis not shown in FIG. 27 as well as by tipping and sliding the light modulator 57 and imaging device 58 or components of the imaging device 58 with respect to one another. It is also possible to reshape the image to generate an undistorted impression in an observer. The latter is possible with both embodiments of FIGS. 26 and 27, alternatively or in addition, by modifying the signal that controls the light modulator 57.

With most of the embodiments presented above with reference to FIGS. 1 through 3 and 15 through 25, it is possible in place of projection surfaces 41 to provide image surfaces that, for example, are configured as rigid or flexible OLED displays in order to emit light and to display information without requiring a projector. Provided that the image surface is not elastic as, for example, in the embodiments in FIGS. 23 through 25, the image surface alternatively can include a rigid liquid crystal display (LCD display), a rigid plasma image screen or another rigid screen.

FIG. 20 shows a schematic depiction of a control device 80 to control one or more functions of the systems, apparatuses and devices that are presented above with reference to FIGS. 1 through 27. The control device is, in particular, coupled with the room camera 24 described above with reference to FIG. 1 and additional room cameras 241, 242, an external image storage device 85, an endoscopy system 69 with an endoscope 691 and a locally sensitive x-ray detector or x-ray sensitive image sensor 622, in order to receive images from them. In addition, the control device 80 can be coupled with the room cameras 24, 241, 242, the endoscopy system 69, 691, the external image storage device 85, an x-ray source 621 and the x-ray sensitive image sensor 622 in order to adjust their operating parameters, to move, pivot and control them.

The control device 80 is also coupled with one or more projectors 50 in order to emit image signals to the projectors 50. In addition, the control device 80 is coupled with power drive devices 44, 54, 64 at projection surfaces, projectors and carrier apparatuses in order to control movements of trolley along one or more tracks as well as translational movements, in particular vertical translation movements, pivoting and rotating movements. The power drive devices 44, 54, 64 and the control device 80 thereby constitute positioning devices to position projection surfaces, projectors, carrier apparatuses or medical devices The control device includes an internal image source 81, a gesture recognition device 82 that is coupled in particular with the room cameras 24, 241, 242 or other sensors, a positioning device 83 and a distortion corrector 84. The gesture recognition 82, positioning 83 and distortion correction 84 can each be achieved partly or completely by separate analog or digital electronic hook-up or partly or completely by software or firmware.

The control device 80 is configured in particular to adjust one or more projection surfaces and one or more projectors or projection systems depending on gestures of medical staff and/or depending on a phase in a work sequence and/or depending on a position or a viewing angle of medical staff, in such a way that medical staff can work under ergonomically favorable conditions. In addition the control device 80 is configured to move or configure projection surfaces, projectors, cameras, carrier apparatuses and other mechanically movable devices in such a way that they do not impede or harm one another and medical staff, and so that a projector and a projection surface, for example, are essentially positioned opposite one another.

The invention claimed is:
1. A ceiling supply system, comprising:
a track device configured to be disposed on a ceiling surface of a medical treatment facility, the track device having a first track determining a first curved path, and a second track determining a second curved path, the first track being equidistantly spaced from the second track along the entire first track;

at least one illumination device disposed between the first track and the second track;

a first trolley slideably connected to only the first track;

a second trolley slideably connected to only the second track; and a carrier apparatus connected to the first trolley, the carrier apparatus including a device holder configured to hold a medical device.

2. The ceiling supply system of claim 1, further comprising a contact track formed of an electrically conductive material in slideable communication with a contact configured to transmit electrical signals between the first trolley and the track device.

3. The ceiling supply system of claim 2, wherein the contact is mounted on the first trolley, and wherein the first trolley further includes an elastic element configured to press the contact against the contact track.

4. The ceiling supply system of claim 1, wherein the device holder is a plate.

5. The ceiling supply system of claim 1, further comprising at least one other illumination device outboard of the first track and the second track.

6. The ceiling supply system of claim 1, wherein the at least one illumination device is configured to direct illumination light down towards an area of the medical treatment facility.

7. The ceiling supply system of claim 1, wherein the carrier apparatus includes a container configured to receive the device holder with the medical device and enclose the medical device in the container; and wherein the device holder is configured to move between an upper resting position inside the container and a lower operating position in which a medical device held by the device holder is configured to be used by medical staff.

8. The ceiling supply system of claim 7, said carrier apparatus further including:

a lifting device configured to move the device holder between the upper resting position and the lower operating position.

9. The ceiling supply system of claim 7, wherein said device holder at least partially closes an opening on the underside of the container in the upper resting position.

10. The ceiling supply system of claim 7, said carrier apparatus further including:

a steering device configured to guide the device holder along a predetermined path between the upper resting position and the lower operating position.

11. The ceiling supply system of claim 10, wherein the steering device includes a scissors mechanism that is configured to hold the device holder in a predetermined orientation regardless of its position.

12. The ceiling supply system of claim 11, wherein the steering device includes a telescopable mechanical connection between the container and the device holder.

13. The ceiling supply system of claim 7, wherein the carrier apparatus includes a rope and a power drive device configured to move the device holder between the upper resting position and the lower operating position using the rope.

14. The ceiling supply system of claim 7, wherein the container is configured to move parallel to the ceiling surface of the medical treatment facility when the track device is disposed on the ceiling surface.

15. The ceiling supply system of claim 7, further comprising a cable to conduct at least either a signal or current or a fluid between the container and the device holder or a medical device held by the device holder.

16. The ceiling supply system of claim 15, further comprising a steering device configured to guide the device holder along a predetermined path between the upper resting position and the lower operating position, wherein the cable is integrated in the steering device or guided on the steering device.

17. The ceiling supply system of claim 1, wherein the first trolley and the second trolley are independently moveable along the first track and the second track, respectively.

18. The ceiling supply system of claim 1, wherein the first trolley and the second trolley are moveable in opposite directions relative to one another.

19. The ceiling supply system of claim 1, wherein the first curved path is an annular path, and the first track completely surrounds the second track.

20. The ceiling supply system to claim 1, said carrier apparatus further comprising:

a supply arm configured to rotate around a site predetermined by a joint on a ceiling surface of the medical treatment facility, such that the supply arm is configured to be coupled at a site at a distance from the joint with the container of the carrier apparatus, and such that the supply arm is configured to transmit at least either a signal or current or a fluid.

21. A ceiling supply system, comprising:

a track device configured to be disposed on a ceiling surface of a medical treatment facility, the track device having a first track determining a first curved path, and a second track determining a second curved path, the first track being equidistantly spaced from the second track along the entire first track;

at least one illumination device disposed between the first track and the second track;

a first trolley slideably connected to only the first track;

a second trolley slideably connected to only the second track; and a carrier apparatus connected to the first trolley, the carrier apparatus including a device holder configured to hold a medical device;

wherein the first trolley and the second trolley are independently moveable along the first track and the second track, respectively;

wherein the first trolley and the second trolley are moveable in opposite directions relative to one another; and wherein the first curved path is an annular path, and the first track completely surrounds the second track.

* * * * *